US007305895B1

(12) United States Patent
Andrews, Jr. et al.

(10) Patent No.: US 7,305,895 B1
(45) Date of Patent: Dec. 11, 2007

(54) BERNOULLI MUSHROOM INLET HOUSING FOR EFFICIENT AIR SAMPLING

(75) Inventors: George A. Andrews, Jr., Fredericksburg, VA (US); William P. Adams, Mechanicsville, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 44 days.

(21) Appl. No.: 11/401,012

(22) Filed: Mar. 29, 2006

Related U.S. Application Data

(63) Continuation-in-part of application No. 11/134,603, filed on May 19, 2005, now Pat. No. 7,111,521.

(51) Int. Cl.
*G01N 1/00* (2006.01)

(52) U.S. Cl. .................................................. 73/863.51

(58) Field of Classification Search ............ 73/863.41, 73/863.51–863.55, 863.58, 863.82, 863.85, 73/864.63–864.67, 863.81
See application file for complete search history.

(56) References Cited

U.S. PATENT DOCUMENTS

| | | | | |
|---|---|---|---|---|
| 540,121 | A * | 5/1895 | Tagliabue | 73/864.65 |
| 3,587,323 | A * | 6/1971 | Benjaminson | 73/863.21 |
| 3,994,170 | A * | 11/1976 | Czarnecki | 73/863.51 |
| 4,174,083 | A | 11/1979 | Mohn | 244/53 |
| 4,442,720 | A * | 4/1984 | Apley et al. | 73/863.31 |
| 4,502,341 | A | 3/1985 | Hall, II | 73/863.01 |
| 4,504,192 | A | 3/1985 | Cyrus et al. | 416/41 |
| 5,172,592 | A | 12/1992 | Fisher | 73/189 |
| 5,237,881 | A * | 8/1993 | Ross | 73/863.12 |
| 5,327,770 | A | 7/1994 | Hindle | 73/1 |
| 5,404,763 | A | 4/1995 | Guggenheim | 73/863.31 |
| 5,709,419 | A | 1/1998 | Roskey | 415/1 |
| 5,924,823 | A | 7/1999 | Palffy | 406/152 |
| 5,955,682 | A | 9/1999 | Faircloth | 73/863.51 |
| 5,993,309 | A | 11/1999 | Howell et al. | 454/16 |
| 6,427,543 | B1 | 8/2002 | Torrison | 73/853.33 |
| 6,867,413 | B2 | 3/2005 | Basch et al. | 250/255 |
| 2003/0070499 | A1* | 4/2003 | Pratt | 73/863.63 |
| 2004/0050183 | A1 | 3/2004 | Schimmoller et al. | 73/863.23 |

OTHER PUBLICATIONS

U.S. Appl. No. 11/134,603, filed May 19, 2005, Andrews, Jr.

* cited by examiner

*Primary Examiner*—Robert Raevis
(74) *Attorney, Agent, or Firm*—Gerhard W. Thielman, Esq.

(57) ABSTRACT

A collection apparatus is provided for receiving a portion of a medium that flows around the apparatus and directing the portion into a collector. The apparatus includes an axisymmetric streamline receiver and a support member. The streamline receiver includes a chamber as well as at least one opening into the chamber that receives the portion. The support member includes an axisymmetric conduit for directing the portion from the chamber towards the collector.

5 Claims, 4 Drawing Sheets

BERNOULLI MUSHROOM INLET HOUSING FOR EFFICIENT AIR SAMPLING

CROSS REFERENCE TO RELATED APPLICATION

The invention is a Continuation-in-Part, claims priority to and incorporates by reference in its entirety U.S. patent application Ser. No. 11/134,603 filed May 19, 2005 now U.S. Pat. No. 7,111,521 titled "Sampling System for Moving Fluid" to George A. Andrews Jr. and assigned Navy Case 96356.

STATEMENT OF GOVERNMENT INTEREST

The invention described herein may be manufactured and used by or for the Government of the United States of America for governmental purposes without the payment of any royalties thereon or therefor.

BACKGROUND

The invention relates generally to the sampling of moving fluids such as moving airflows, and more particularly to a sampling system that extracts samples of a moving fluid passing thereover.

Moving fluids such as airflows frequently must be sampled for a variety of flow monitoring applications. Such sampling may be performed to examine the ambient air for chemical, biological and/or radiological particulates. Other purposes may include inertial characteristics of the airflows, such as provided by pressure measurements.

A typical sampling system incorporates a housing having an inlet formed therein and a pump or fan. The inlet faces directly into the flowstream, and the fluid expands into a diffuser before being diverted to a collector. As fluid (e.g., air) moves over the housing, the pump draws the fluid into the housing through the inlet and toward the collector. The inlet and pump may be optimized for an expected set of external flow conditions. In particular, the system can be designed for appropriate pump power consumption and pump speeds under the expected fluid flow conditions.

However, if the fluid flow speed significantly exceeds the design parameters, the Bernoulli effect at the housing's inlet causes backpressure to develop in the housing. Bernoulli's principle concerns the relationship between static and dynamic pressures, such that $P_0=P+\frac{1}{2}?u^2$, where $P_0$ represents stagnation or total pressure (of fluid being at rest), P is static pressure (parallel to fluid flow), ? is fluid density and u is fluid velocity.

As the fluid enters the housing, the velocity decreases, thereby increasing static pressure inside the housing. The difference between the internal housing static pressure and the external static pressure in the ambient stream represents the backpressure. As the backpressure increases within the housing, the pump must rotate faster than its design operational levels to draw the moving fluid into the collector. Such continued beyond-design operation may yield decreased pump efficiency and increased risk of motor overheating.

SUMMARY

Conventional medium collection inlets yield disadvantages addressed by various exemplary embodiments of the present invention. In particular, various embodiments mitigate against backpressure inefficiency, as well as reduce inlet friction loss. Other various embodiments alternatively or additionally provide for omnidirectional flow receipt within a horizontal plane.

Various exemplary embodiments provide an axisymmetric collection apparatus for receiving a portion of a medium that flows around the apparatus and directing the portion into a collector. The apparatus includes an axisymmetric streamline receiver and a support member. The receiver contains a chamber and at least one opening into the chamber that receives the portion. The support member includes an axisymmetric conduit for directing the portion from the chamber towards the collector.

In various exemplary embodiments, the opening has an annular axisymmetric geometry. In alternate embodiments, the opening represents a plurality of openings angularly distributed along an exterior surface of the streamline receiver, each opening having a finite angular width. The axisymmetric conduit may direct a subportion of the portion to a diversion opening that encompasses an axial centerline of the streamline receiver.

Various exemplary embodiments also provide a planform collection apparatus for receiving a portion of a medium that flows around the apparatus and directing the portion into a collector. The apparatus includes a streamline receiver, a support member and a tail stabilizer. The receiver includes upper and lower members that form leading and trailing edges to define a chord.

At least one of the members incorporates along an exterior surface at least one opening that receives the portion. The support member has a conduit that directs the portion from the opening towards the collector. The tail stabilizer may be secured to the streamline receiver for orienting the leading edge into the medium.

In various embodiments, the opening includes an interior surface recessed from the exterior surface. In further embodiments, the interior surface slants to deepen with the distance from the leading edge. In additional embodiments, the opening includes boundary walls that define the varying width, and the boundary walls connect to the interior surface.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which.

DETAILED DESCRIPTION

Conventional inlet designs for fluid sample collection housings are subject to the following limitations: First, Bernoulli-effect backpressure in a housing at off-design fluid flowspeeds reduces collection efficiency and may adversely affect pump operational life. Second, boundary layer thickness development within the inlet influences fluid flow into the housing. Third, an inertial response time for weathervane directional alignment to the fluid flow. Various exemplary embodiments address these limitations in the conventional configurations.

Figure 1:
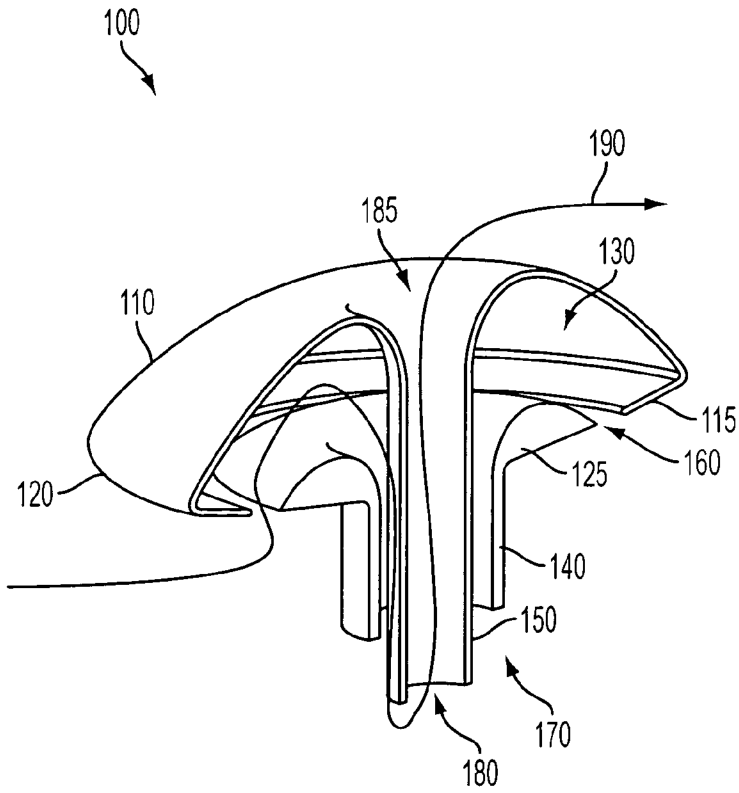
FIG. 1 is an isometric cross-section view of an axisymmetric mushroom inlet assembly.

FIG. 1 shows an isometric cross-sectional view of a first omnidirectional sampling inlet structure 100 that is axisymmetric about a substantially vertical symmetry axis. An outer mushroom-shape aeroshell 110 presents a streamline plan profile over which a medium (e.g., especially ambient air, but alternatively water, oil and other gasses or liquids) passes as a flowfield from a horizontal transverse direction within a substantially horizontal omnidirectional plane. An outer-under rim 115 forms a lower lip connecting to the streamline body or aeroshell receiver 110 at a joining circumference 120 along the maximum outer diameter.

The passing medium impinges the structure 100 at a leading edge within the flowfield approximately at the joining circumference 120. An inner-under planform 125 provides a surface under which the flowfield passes along the transverse direction. The volume substantially enclosed above by the aeroshell 110 and below by the rim 115 and the planform 125 forms a chamber 130 into which the medium may enter.

The planform 125 may be supported by a cylindrical outer stem 140 substantially parallel to the symmetry axis. A cylindrical inner stem 150, also substantially parallel to the symmetry axis may support the aeroshell 110. The stems 140, 150 may be tilted together in association with the symmetry axis in an off-vertical direction for reorienting the structure 100.

As the flowfield passes over and under the structure 100, a flow portion of the medium passes into an annular inlet 160 formed between the rim 115 and the planform 125 into the chamber 130. The outer and inner stems 140, 150 form an annular channel 170 directing the flow portion from the chamber 130 therethrough.

The aeroshell 110 may be represented geometrically by an upper (or top) profile having a first radius of curvature. A contiguously assembled surface containing the rim 115, the inlet 160 and the planform 125 may be represented geometrically by a lower (or bottom) profile having a second radius of curvature. To minimize back pressure within the chamber 130, the structure 100 may enable a higher static pressure below the structure and adjacent the inlet 160 than above the structure. Under the Bernoulli principle then, the flowfield velocity over the aeroshell 110 preferably exceeds the velocity under the contiguously assembled surface. Consequently, the first radius of curvature may preferably be smaller than the second radius of curvature, such that the lower profile appears flatter than the upper profile. The upper and lower profiles are revolved about the symmetry axis to form the axisymmetric structure 100.

Particulate matter entrained within the flow portion may sweep on (downward) past the annular inlet 170 into a collector (not shown) by inertia and drag of the individual particles. The collector may represent a "dry filter unit" (DFU) used to detect selectable particulates for chemical or biological analysis. The remaining flow portion may be redirected (upward) towards a tube 180 formed by the inner stem 150 and ejected from the structure 100 through an outlet 185. An example streamline 190 traces a path through which an entering portion of the medium may traverse.

As a consequence of the flow paths into the inlet and ejected through the outlet 185, the backpressure equilibrates to the ambient conditions, thereby reducing flow inefficiency. Moreover, the axisymmetric design of the structure 100 permits medium reception from omnidirectionally within the substantially horizontal flow plane.

Figure 2:
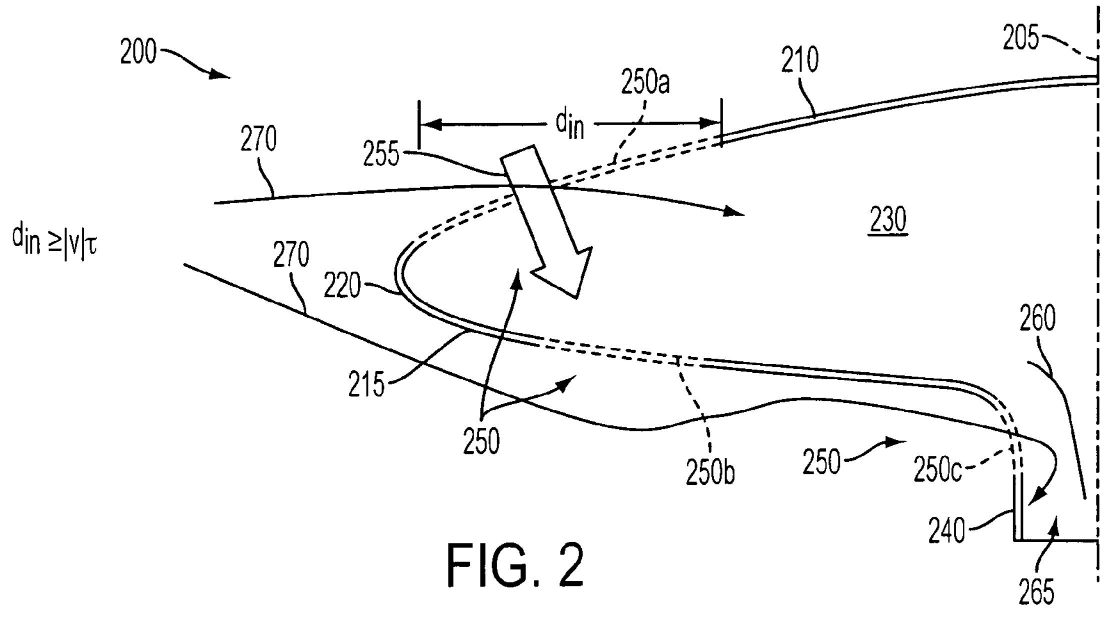
FIG. 2 is a plan cross-section diagram of an inlet assembly having an axisymmetric airfoil.

FIG. 2 shows a plan cross-sectional view of a second omnidirectional sampling inlet structure 200 that is axisymmetric about a substantially vertical symmetry axis 205. An upper airfoil shell 210 presents a plan profile over which the medium passes as a flowfield from a horizontal transverse direction substantially perpendicular to the symmetry axis 205. A lower airfoil shell 215 presents a plan profile under which the medium passes and connects to the upper airfoil shell 210 at a joining circumference 220 along the maximum outer diameter.

The passing medium impinges the structure 200 at a leading edge within the flowfield approximately at the joining circumference 220. The volume substantially enclosed by the shells 210, 215 forms a chamber 230 into which the medium may enter. In context of the exemplary embodiments described herein, the term "airfoil" denotes a streamline shape within a flowfield in which the medium may preferably be but not limited to atmospheric air.

A cylindrical outer stem 240 parallel to the symmetry axis may support the lower airfoil shell 215. The stem 240 may be tilted in association with the symmetry axis 205 in an off-vertical direction for reorienting the structure 200. As the flowfield passes over and under the structure 200, a flow portion of the medium passes into at least one annular inlet 250.

Each inlet 250 may form either a substantially annular opening circumferentially around the symmetry axis 205. Alternatively, each inlet 250 may represent a series of openings into the chamber 230 having finite angular width and being angularly distributed around the symmetry axis 205.

The inlets 250 may be characterized by an effective radial length din locally tangent to the structure 200. The radial length is normal to the flow direction 255 and must be at least equal an absolute velocity |v| of the flow times a characteristic time constant t. The inlets 250 may additionally, or in the alternative, employ Bernoulli-effect principles described further below.

The upper airfoil shell 210 may include an inlet 250*a*, as above described for an annular ring or a series. The lower airfoil shell 215 may include an inlet 250*b*, also as an annular ring or a series. The outer stem 240 may include, near its juncture with the lower airfoil shell 215, an inlet 250*c*, also as an annular ring or a series.

As the medium flows around the structure 200, a portion of the flow enters the chamber 230 through the inlets 250, traveling radially inward. A baffle or diverter 260 redirects the flow portion downward into the outer stem 240 towards a tube channel 265 to enter a collector (not shown). Example streamlines 270 show the path of the flow portion entering the inlets 250 and diverting to the tube channel 265 for analysis.

Figure 3A:
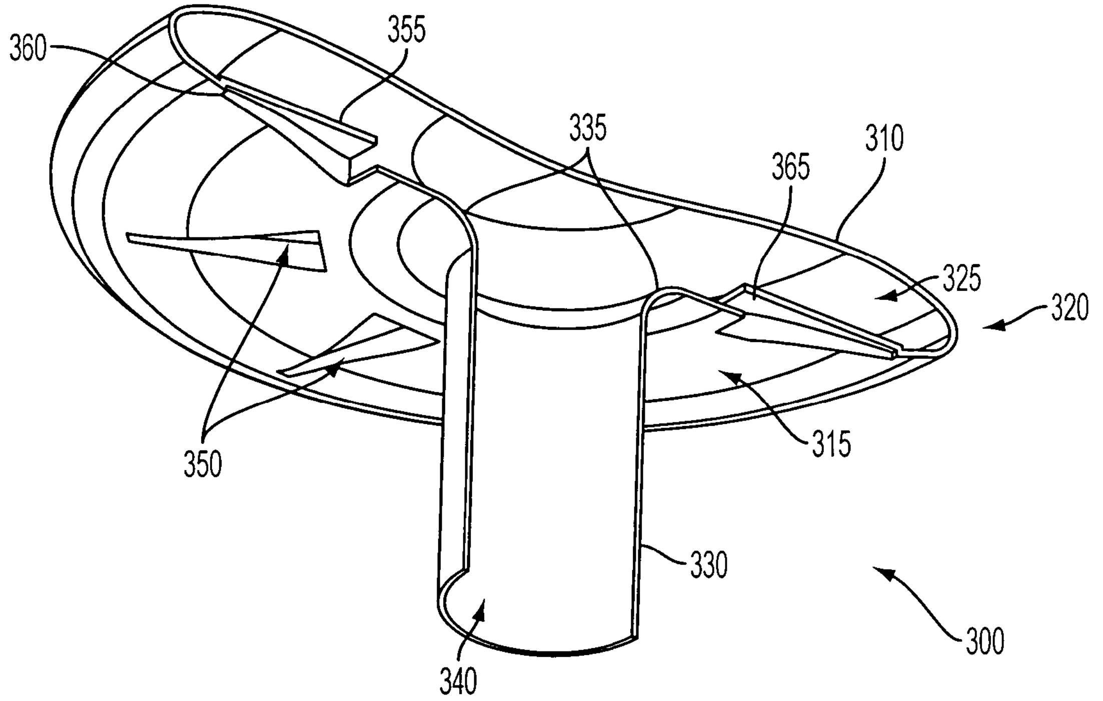
FIGS. 3A and 3B are cross-section isometric views of an inlet assembly having an axisymmetric airfoil and Bernoulli-effect inlets.
Figure 3B:
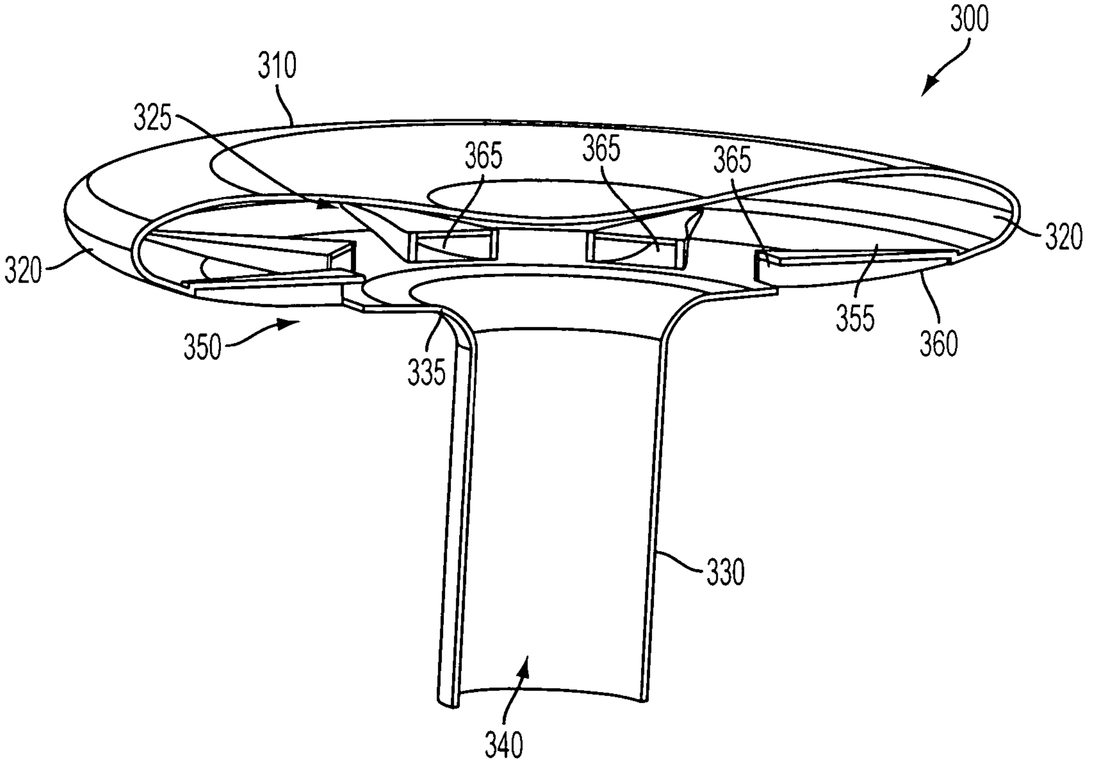

FIGS. 3A and 3B show isometric cross-sectional views of a second omnidirectional sampling inlet structure 300 that is axisymmetric about a substantially vertical symmetry axis. A circumferential upper shell 310 exhibits an airfoil cross-section about the symmetry axis extending along a top surface of the structure 300. A circumferential lower shell 315 presents a comparatively flat cross-section about the symmetry axis extending along a bottom surface of the structure 300.

The upper and lower shells 310, 315 converge to join along a circumferential rim 320, thereby enclosing a chamber 325 for the structure 300. FIGS. 3A and 3B present the views of the structure 300 from below and above the rim 320, respectively. The medium can flow from any horizontal direction transverse to the symmetry axis over the upper shell 310 and under the lower shell 315. The lower shell 315 may be supported by a cylindrical stem 330 and joined circumferentially along a fillet 335 to form a tube 340 parallel to the symmetry axis.

Several inlets 350 may be circumferentially distributed along the lower shell 315 to permit the medium to flow into the chamber 325. Alternatively, the inlets 350 may be circumferentially distributed along the upper shell 310, particularly for collective inclusion of precipitation. Each inlet 350 includes a recessed surface 355 within the chamber 325. The recessed surface 355 may be substantially perpendicular to the symmetry axis, thereby being approximately parallel to streamlines entering the inlet 350.

The inlet 350 benefits from the Bernoulli effect by employing a narrow shallow opening at an outer radius end 360 and a wide deep opening at an inner radius end 365. The outer and inner radii refer to structure 300 from the symmetry axis. The widths between these openings 360, 365 may vary linearly, or nonlinearly, such as the flat-Gaussian curve shown. This geometry enables the boundary layer within the inlet 350 to remain substantially uniform, thereby reducing pressure losses into the structure 300. This design opening is labelled a "Bernoulli-effect inlet" herein.

A boundary layer develops along the surface 355 as the medium flows into the inlet 350. Expansion of the depth and width of the inlet 350 as the medium to flow progressively into the chamber 325 reduces viscous drag losses, thereby reducing pressure drop across the inlet as well as turbulence. The medium flows towards the radial center of the structure 300 and turns downward into the tube 340 to enter a collector (not shown).

Figure 4:
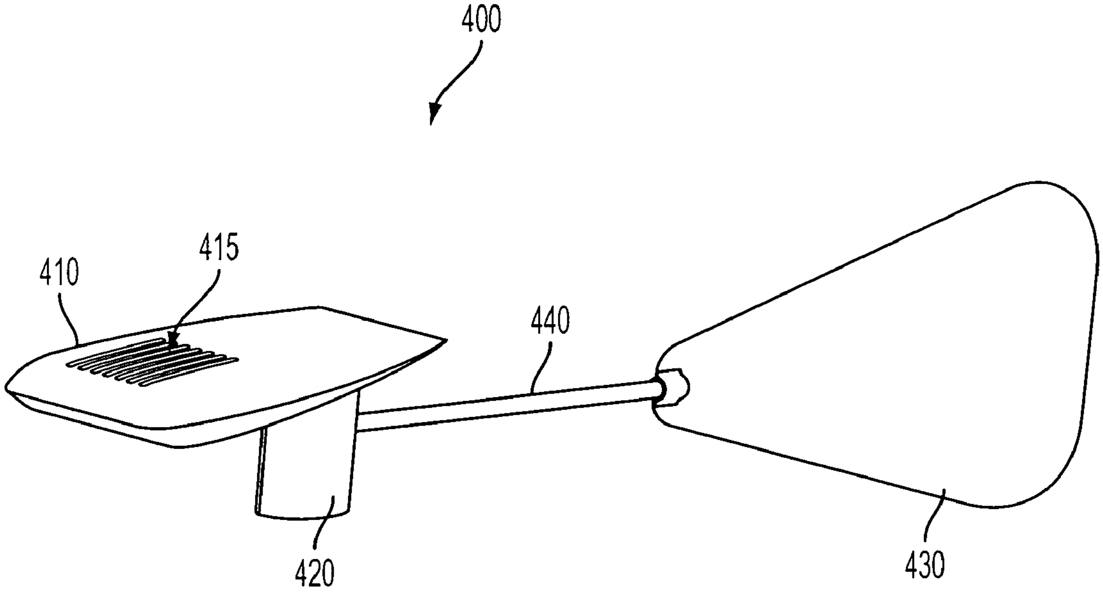
FIG. 4 is an isometric view of a weathervane inlet system.

FIG. 4 shows an isometric view of a weather-vane sampling inlet assembly 400. The assembly 400 features an airfoil 410 having slit inlets 415 supported on a strut 420 leading into a collector (not shown). The strut 420 may be oriented in a substantially vertical direction to enable the airfoil 410 to rotate toward any direction in a substantially horizontal plane. The inlets 415 have lengths at least an order of magnitude greater than the corresponding widths.

The assembly 400 may further include a tail 430 that orients the assembly 400 to direct the airfoil 410 towards windward by connection to a stiff linkage or rod 440 in the manner of a weathervane. The airfoil 410 may represent cross-section planforms documented by the former National Advisory Committee for Aeronautics (NACA). Many NACA planforms are bilaterally symmetric across the chord. This embodied configuration is described in U.S. patent application Ser. No. 11/134,603 incorporated by reference.

Figure 5A:
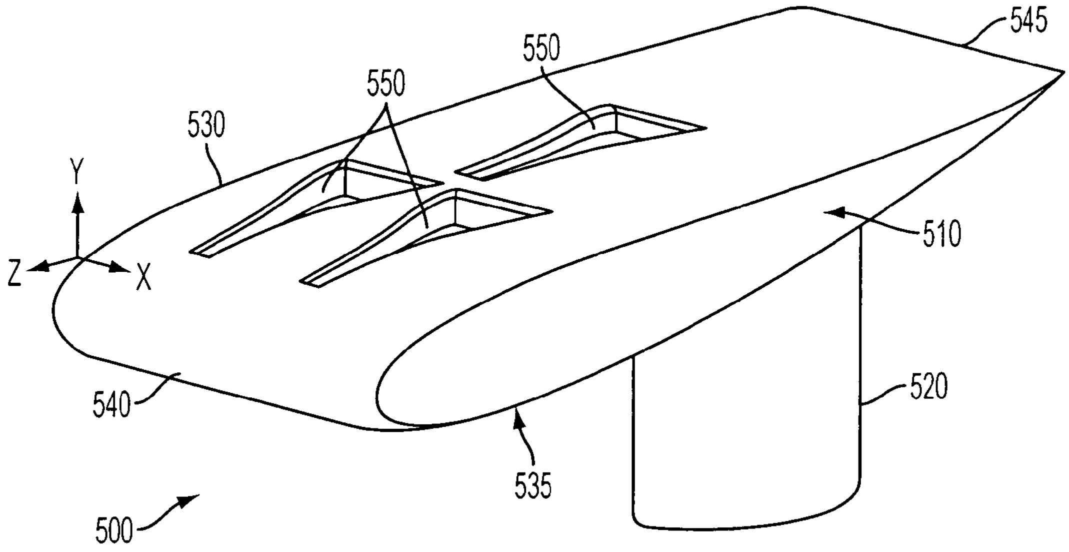
FIGS. 5A and 5B are isometric views of a weathervane inlet airfoil having Bernoulli-effect inlets, with FIG. 5B representing a cross-section view.
Figure 5B:
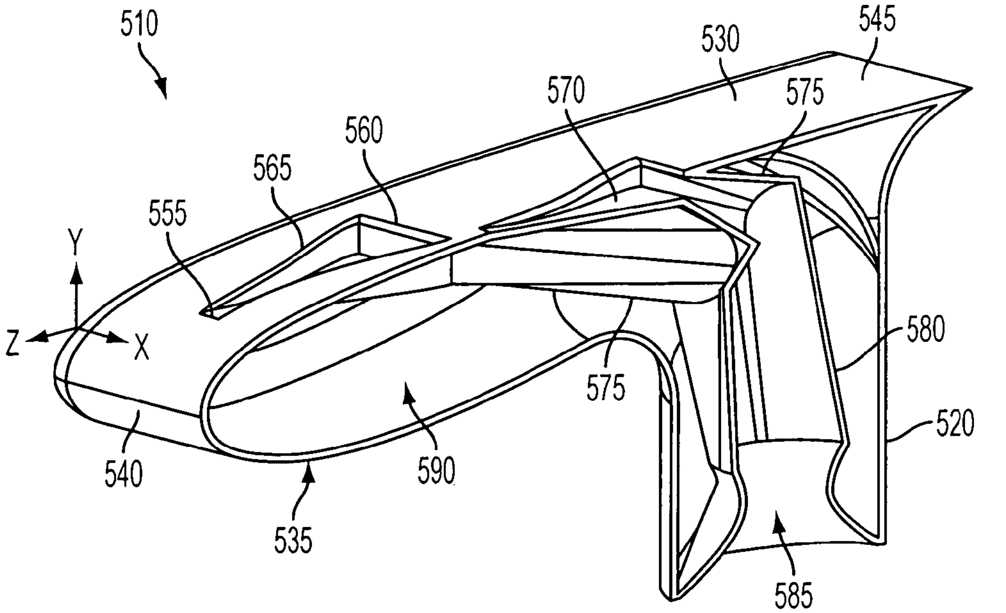

FIGS. 5A and 5B shows isometric views of a weather-vane sampling inlet system 500 in similar fashion to the assembly 400 shown in FIG. 4 but absent explicit illustration of the tail 430 and the rod 440. FIG. 5A represents an airfoil 510 supported on a stem 520 as viewed from above. In a similar view, FIG. 5B represents a chord-wise cross-section of the airfoil 510 showing its interior across its midspan.

The airfoil 510 provides an upper surface 530 and a lower surface 535 exposed to the medium. At a forward end, the surfaces 530, 535 may be joined at a leading edge 540. Similarly at the aft end, the surfaces 530, 535 may be joined at a trailing edge 545. These surfaces and edges may represent NACA planforms. The leading and trailing edges 540, 545 form a chord of the airfoil 510.

The system 500 differs from the assembly 400 primarily by employment of Bernoulli-effect inlets 550. FIG. 5A shows the inlets 550 on the upper surface 530, although the inlets may also be employed on the lower surface 535. Each inlet 550, as shown in FIG. 5B, employs a narrow shallow forward end 555 and a wide deep aft end 560. The aft end 560 is farther downstream from the leading edge 540 than the forward end 555.

A portion of the medium that flows over the airfoil 510 may enter the inlet 550. The portion flows between recessed walls 565 that define the forward and aft ends 555, 560 and along a recessed surface 570 to contain a boundary layer region of the portion. The recessed surface 570 may be substantially parallel to the chord, or alternatively may be slanted to provide a deeper channel at the aft end 560 than the forward end 555. The widths between these ends 555, 560 may vary linearly, or nonlinearly, such as the flat-Gaussian curve shown.

A chute 575 connected downstream (i.e., aft) of the associated inlet 550 directs the flow portion into a channel 580 within the strut 520. The chute 575 may join contiguously with the recessed walls 565 and the recessed surface 570. The channel 580 leads to a conduit 585 into a collector (not shown).

A chamber 590 represents interior regions not in communication with the inlet 550, the chute 575 or the channel 580. Thus, in the depicted exemplary version, the flow portion does not enter the chamber 590, which may be vented to equilibrate with an appropriate pressure level relative to ambient conditions to maintain structural integrity and/or internal chamber pressure for optimal inlet flow performance.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A collection apparatus for receiving a portion of a medium that flows around the apparatus and directing the portion into a collector, the apparatus comprising:

an axisymmetric streamline receiver that houses a chamber, the streamline receiver having a plurality of openings into the chamber that receives the portion; and a support member having an axisymmetric conduit for directing the portion from the chamber towards the collector, wherein the streamline receiver and the support member share a rotational axis of symmetry substantially perpendicular to a flow direction of the medium, at least one opening of the plurality of openings is oriented substantially parallel to the flow direction, and the plurality of openings are angularly distributed along an exterior surface of the streamline receiver, each opening having an acute annular width.

2. The apparatus according to claim 1, wherein the angular width increases as a radius of the streamline receiver decreases.

3. The apparatus according to claim 1, wherein the each opening includes a boundary surface substantially perpendicular to an axial centerline of the streamline receiver and disposed within the chamber of the streamline receiver.

4. The apparatus according to claim 1, wherein the streamline receiver includes upper and lower planforms, and the plurality of angularly distributed openings includes at least one of a first plurality distributed on the upper planform and a second plurality distributed on the lower planform.

5. The apparatus according to claim 4, further comprising a third plurality of openings distributed on the support member.

* * * * *